(12) United States Patent
Lee et al.

(10) Patent No.: US 11,589,739 B2
(45) Date of Patent: Feb. 28, 2023

(54) APPARATUS AND METHOD FOR ACQUIRING NEAR INFRARED-BASED DIAGNOSTIC IMAGES OF TEETH

(71) Applicant: KOREA PHOTONICS TECHNOLOGY INSTITUTE, Gwangju (KR)

(72) Inventors: Byeong-Il Lee, Busan (KR); In-Hee Shin, Gwangju (KR)

(73) Assignee: KOREA PHOTONICS TECHNOLOGY INSTITUTE, Gwangju (KR)

( * ) Notice: Subject to any disclaimer, the term of this patent is extended or adjusted under 35 U.S.C. 154(b) by 754 days.

(21) Appl. No.: 16/545,893

(22) Filed: Aug. 20, 2019

(65) Prior Publication Data
US 2019/0365237 A1    Dec. 5, 2019

Related U.S. Application Data

(63) Continuation of application No. PCT/KR2018/000771, filed on Jan. 17, 2018.

(30) Foreign Application Priority Data

Jun. 14, 2017  (KR) .................. 10-2017-0074574

(51) Int. Cl.
*A61B 1/04*     (2006.01)
*H04N 5/232*    (2006.01)
(Continued)

(52) U.S. Cl.
CPC ............ *A61B 1/04* (2013.01); *A61B 1/00009* (2013.01); *A61B 1/046* (2022.02); *A61B 1/24* (2013.01); *A61B 5/0088* (2013.01); *A61B 5/1111* (2013.01); *G06T 7/0012* (2013.01); *H04N 5/2256* (2013.01); *H04N 5/23238* (2013.01); *H04N 5/23299* (2018.08); *A61B 2562/0247* (2013.01); *G06T 2207/10048* (2013.01); *G06T 2207/30036* (2013.01)

(58) Field of Classification Search
CPC ................ A61B 5/0088; A61B 5/1111; G06T 2207/10048; G06T 2207/30036; G06T 7/0012; H04N 5/23299; H04N 5/2256
See application file for complete search history.

(56) References Cited

U.S. PATENT DOCUMENTS

2005/0202363 A1* 9/2005 Osterwalder ........ A61C 19/066
                                                    433/29

FOREIGN PATENT DOCUMENTS

JP     2001024750     *  7/2001
JP     2001204750     *  7/2001
(Continued)

OTHER PUBLICATIONS

International Search Report issued in PCT/KR2018/000771; dated May 18, 2018.

*Primary Examiner* — Kathleen V Nguyen
(74) *Attorney, Agent, or Firm* — Studebaker & Brackett PC

(57) ABSTRACT

The present invention relates to an apparatus and a method of acquiring an image for dental diagnosis. More particularly, the present invention relates to an apparatus and a method of acquiring a near-infrared image for dental diagnosis, wherein an image for dental diagnosis is acquired using near-infrared radiation and a general image camera rather than using X-rays.

9 Claims, 8 Drawing Sheets

(51) Int. Cl.
    *A61B 1/24*     (2006.01)
    *A61B 5/00*     (2006.01)
    *A61B 5/11*     (2006.01)
    *G06T 7/00*     (2017.01)
    *H04N 5/225*     (2006.01)
    *A61B 1/00*     (2006.01)

(56) References Cited

FOREIGN PATENT DOCUMENTS

| | | | |
|---|---|---|---|
| JP | 2012-125455 A | | 7/2012 |
| JP | 2012125455 | * | 7/2012 |
| JP | 2005270143 | * | 10/2015 |
| JP | 2016-214427 A | | 12/2016 |
| KR | 10-2015-0021310 A | | 3/2015 |
| KR | 101651255 | * | 8/2016 |

\* cited by examiner

APPARATUS AND METHOD FOR ACQUIRING NEAR INFRARED-BASED DIAGNOSTIC IMAGES OF TEETH

CROSS-REFERENCE TO RELATED APPLICATIONS

The present application is a continuation of International Patent Application No. PCT/KR2018/000771, filed Jan. 17, 2018, which is based upon and claims the benefit of priority to Korean Patent Application No. 10-2017-0074574, filed on Jun. 14, 2017. The disclosures of the above-listed applications are hereby incorporated by reference herein in their entirety.

TECHNICAL FIELD

The present invention relates to an apparatus and a method of acquiring an image for dental diagnosis. More particularly, the present invention relates to an apparatus and a method of acquiring a near-infrared image for dental diagnosis, wherein an image for dental diagnosis is acquired using near-infrared radiation and a general image camera rather than using X-rays.

BACKGROUND ART

Generally, in dentistry, before a dental treatment, a mouth portion of a patient is subjected to radiography such that an X-ray image showing patient's teeth structure and condition is acquired.

The dental X-ray image may show information on cavities and voids of the dental tissue, and information on a desalinized portion in which the mineral components of the dental tissue have been removed and the tissue is porous.

In X-ray imaging, emptied or desalinized portions transmit X-rays more than nearby tissue and transmit X-rays with higher intensity radiated from the source more than the nearby tissue. More exposure occurs to the photographic films or the electronic imaging devices due to the emptied or desalinized portions than exposure formed by the radiation coming along the path that the emptied or desalinized portions do not block.

Typically, such an X-ray method has several disadvantages. X-rays are dangerous because X-rays ionize molecules of living tissue. When the cavity area is empty, this is completely transparent. However, the cavities with a small volume having higher permeability or lower attenuation make only a small partial change in the intensity of the transmitted radiation, so that for the portion of the small cavities, contrast in the X-ray image is poor. Therefore, it is difficult to detect cavities with a small volume from general X-ray images. Nevertheless, the cavities occurring in the edge portion of the tooth may often be detected. On the other hand, in general, there is a problem in that it is difficult to find occlusal cavities on the wide and flat chewing surfaces.

In addition to when searching for cavities, dentists need a means for detecting cracks in teeth when replacing old fillings, when deciding whether to use another inlay, and when deciding whether to use a crown. However, the X-ray method has a problem that the reliability for detecting cracks is poor.

DISCLOSURE

Technical Problem

Accordingly, an object of the present invention is intended to propose an apparatus and a method of acquiring a near-infrared image for dental diagnosis, wherein an image for dental diagnosis is acquired using near-infrared radiation and a general image camera rather than using X-rays.

Technical Solution

In order to achieve the above object, according to the present invention, there is provided an apparatus for acquiring a near-infrared image for dental diagnosis, the apparatus including: a dental diagnosis module inserted into a patient's mouth, the dental diagnosis module including a near-infrared light source that is placed along a teeth arrangement in an inner side of the patient's teeth and radiates near-infrared radiation in an outward direction of the patient's mouth; an optical camera placed in front of a patient's face to photograph the mouth, the optical camera photographing the near-infrared radiation that is radiated from the near-infrared light source and penetrates toward outside of the patient's mouth, and outputting the near-infrared image; and a control module generating a near-infrared teeth arrangement image from the near-infrared image input from the optical camera and outputting the near-infrared teeth arrangement image.

The dental diagnosis module may be configured to, be provided in a shape of a mouthguard and include multiple near-infrared light sources on a surface thereof in contact with an inner surface of the teeth, and be provided with a pressure sensor for each tooth at a portion thereof in contact with a chewing surface of each tooth so as to measure a bite pressure for each tooth of at least one among an upper teeth arrangement and a lower teeth arrangement, and the control module may be configured to, further generate a bite pressure image of the upper teeth arrangement and the lower teeth arrangement from the bite pressure and output the bite pressure image.

The apparatus may further include a camera moving unit, on which the optical camera is placed, moving the optical camera to a front side of the patient's face, from the front side of the patient's face to a left side of the patient's face and to a right side of the patient's face, wherein the control module may be configured to, acquire a front-side near-infrared image, a left-side near-infrared image, and a right-side near-infrared image while moving the optical camera to the front side, the left side, and the right side of the patient's face through the camera moving unit, and construct a panoramic image using the front-side near-infrared image, the left-side near-infrared image, and the right-side near-infrared image so as to generate the near-infrared teeth arrangement image and output the near-infrared teeth arrangement image.

The control module may include: an image processing unit connected to the optical camera, the image processing unit processing the near-infrared image input from the optical camera in a preset image format and outputting the processed near-infrared image; a transport processing unit outputting a driving signal to the camera moving unit so as to control a movement direction and a movement speed of the camera moving unit; a diagnosis module driving unit outputting a near-infrared radiation driving signal and a pressure sensor driving signal to the dental diagnosis module, and receiving a pressure value for each tooth, which results from the pressure sensor driving signal, from the dental diagnosis module to output the pressure value for each tooth; a display unit displaying information as at least one among text, a graphic, and an image; and a control unit configured to: receive, from the image processing unit, the front-side near-infrared image, the left-side near-infrared image, and the right-side near-infrared image, construct the panoramic image to generate a dental image, and output the dental image through the display unit; and measure the bite pressure which is the pressure value for each tooth input through the diagnosis module driving unit, generate the bite pressure image for the measured bite pressure, and output the bite pressure image through the display unit.

The control unit may include: a module control unit controlling the diagnosis module driving unit to drive the dental diagnosis module; a camera position control unit controlling a position of the optical camera by controlling the transport processing unit according to preset optical camera position information; an image acquisition unit acquiring, when the dental diagnosis module is driven through the module control unit and the position of the optical camera is set, the front-side near-infrared image, the left-side near-infrared image, and the right-side near-infrared image input through the image processing unit (450) in order of movement of the optical camera, and outputting the front-side, the left-side, and the right-side near-infrared image; a teeth arrangement image generation unit generating the near-infrared teeth arrangement image by assembling the front-side near-infrared image, the left-side near-infrared image, and the right-side near-infrared image, which are acquired through the image acquisition unit, into the panoramic image, and outputting the near-infrared teeth arrangement image; a bite pressure collection unit collecting the bite pressure for each tooth through the diagnosis module driving unit; and a bite pressure image generation unit generating the bite pressure image based on the bite pressure collected through the bite pressure collection unit and on the near-infrared teeth arrangement image, and outputting the bite pressure image.

The teeth arrangement diagnosis module may include: a frame in a shape of a mouthguard, the frame having: a light source composition unit defining a surface of the frame in the shape of the mouthguard, the surface being in contact with an inner surface of the teeth arrangement, and a sensor composition unit defining a surface that is vertically connected with the light source composition unit and is in contact with a chewing surface of the tooth of the teeth arrangement; an infrared light source array including multiple near-infrared light sources arranged on the light source composition unit of the frame, the multiple near-infrared light sources simultaneously radiating near-infrared radiation from an inner side of the mouth in the outward direction; a pressure sensor array provided on the sensor composition unit of the frame, the pressure sensor measuring a bite pressure, which is a pressure applied by each tooth, and outputting the bite pressure; a battery provided inside the frame and supplying source power; a light source driving unit provided inside the frame, the light source driving unit receiving the source power to supply driving power to the infrared light source array; a pressure measurement unit provided inside the frame, the pressure measurement unit receiving the source power to supply sensor driving power to the pressure sensor array, measuring the bite pressure, which is a pressure value for each tooth corresponding thereto, and outputting the bite pressure; a wireless communication unit provided inside the frame, the wireless communication unit transmitting information over a wireless signal, detecting information contained in a received wireless signal, and outputting the information; and a diagnosis module control unit provided inside the frame, the diagnosis module control unit controlling, when a dental diagnosis module driving signal is received through the wireless communication unit, the light source driving unit to cause the near-infrared light sources through the infrared light source array to radiate, and receiving the bite pressure through the pressure measurement unit to transmit the bite pressure to the control module through the wireless communication unit. The control module may be configured to, transmit a teeth arrangement diagnosis module driving signal in a wireless manner when a teeth arrangement diagnosis module driving event is generated, and receive the bite pressure in a wireless manner to generate a bite pressure image.

The control unit may be configured to, measure a twist of the teeth and periodontium from the near-infrared teeth arrangement image, generate a teeth arrangement image including information on the measured twist, and display the teeth arrangement image through the display unit.

In order to achieve the above object, according to the present invention, there is provided a method of acquiring a near-infrared image for dental diagnosis, the method including: a dental diagnosis module driving process in which a dental diagnosis module inserted into a patient's mouth is driven and a near-infrared light source placed along a teeth arrangement in an inner side of the patient's teeth is driven to radiate near-infrared radiation; a near-infrared image acquisition process in which an optical camera placed in front of a patient's face is driven to photograph the near-infrared radiation that is radiated from the inner side of patient's teeth and penetrates, and the near-infrared image is output; and a dental image acquisition process in which a near-infrared teeth arrangement image is generated from the near-infrared image and is output.

The dental diagnosis module driving process may include: a near-infrared radiation step in which an array of multiple near-infrared light sources provided on a surface, which is in contact with an inner surface of the teeth arrangement, of the dental diagnosis module provided in a shape of a mouthguard is driven to radiate the near-infrared radiation from the inner side of the teeth in an outward direction; and a pressure sensor driving step in which a pressure sensor is driven that is provided at a portion of the dental diagnosis module, the portion being in contact with a chewing surface of each tooth. The image acquisition process may include: a near-infrared teeth arrangement image acquisition step in which a near-infrared teeth arrangement image is generated from the near-infrared image and is output; and a bite pressure image acquisition step in which bite pressure images of an upper teeth arrangement and a lower teeth arrangement are generated from a bite pressure and are output.

The image acquisition process may include: a front-side photographing step in which the optical camera is positioned in front of the patient and photographs the near-infrared radiation at a front side of the patient; and a flank-side photographing step in which the optical camera is moved to left and right sides sequentially and photographs the near-infrared radiation with respect to each of the left side and the right side. At the near-infrared teeth image acquisition step, the front-side, left-side, and right-side near-infrared images may be assembled in a panoramic manner to generate and output the near-infrared teeth arrangement image.

The image acquisition process may further include a teeth/periodontium twist information generation step in which the near-infrared teeth arrangement image is analyzed to measure a twist of the teeth and periodontium and a near-infrared teeth arrangement image containing teeth and periodontium twist information having a measured twist value of the teeth and the periodontium is generated and is output.

Advantageous Effects

According to the present invention, near-infrared radiation is used rather than X-rays, so that the risk of ionization caused by radiation can be eliminated, and safety and reliability for the apparatus can be provided to the patient.

Also, according to the present invention, since near-infrared radiation is used, it is easy to find occlusal cavities on teeth, or the like.

Also, according to the present invention, a panoramic image is implemented using images acquired at different angles, so that the degree of twisting of teeth/periodontal axes, the degree of occlusion, or the like are quantified for dental diagnosis.

Also, according to the present invention, by applying the mouthguard-shaped dental diagnosis module provided with the pressure sensor, the bite pressure when the mouthguard-shaped dental diagnosis module is bitten down on can be measured and can be imaged, whereby the bite pressure distribution for each tooth can be obtained and the hardness for each tooth, and the like are quantified for dental diagnosis.

Also, according to the present invention, a near-infrared light source, a pressure sensor, and a general image camera are used, so that the production cost and the sales price of the apparatus for acquiring a dental image can be lowered.

DETAILED DESCRIPTION

Hereinafter, a configuration and an operation of an apparatus for acquiring a near-infrared image for dental diagnosis according to the present invention will be described with reference to the accompanying drawings, and a method of acquiring the image for dental diagnosis, which is performed by the apparatus, will be described.

Figure 1:
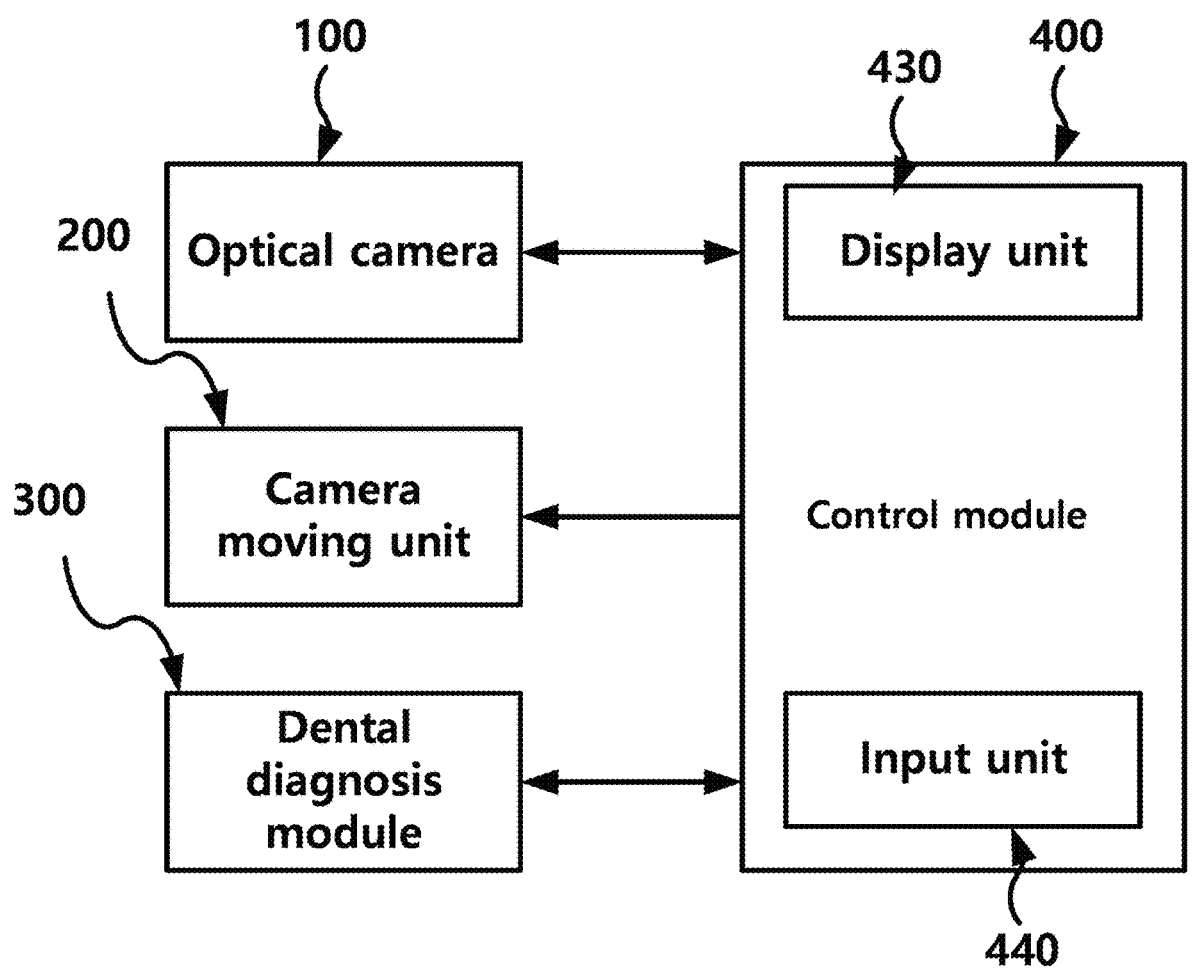
FIG. 1 is a diagram illustrating a configuration of an apparatus for acquiring a near-infrared image for dental diagnosis according to the present invention.
Figure 2:
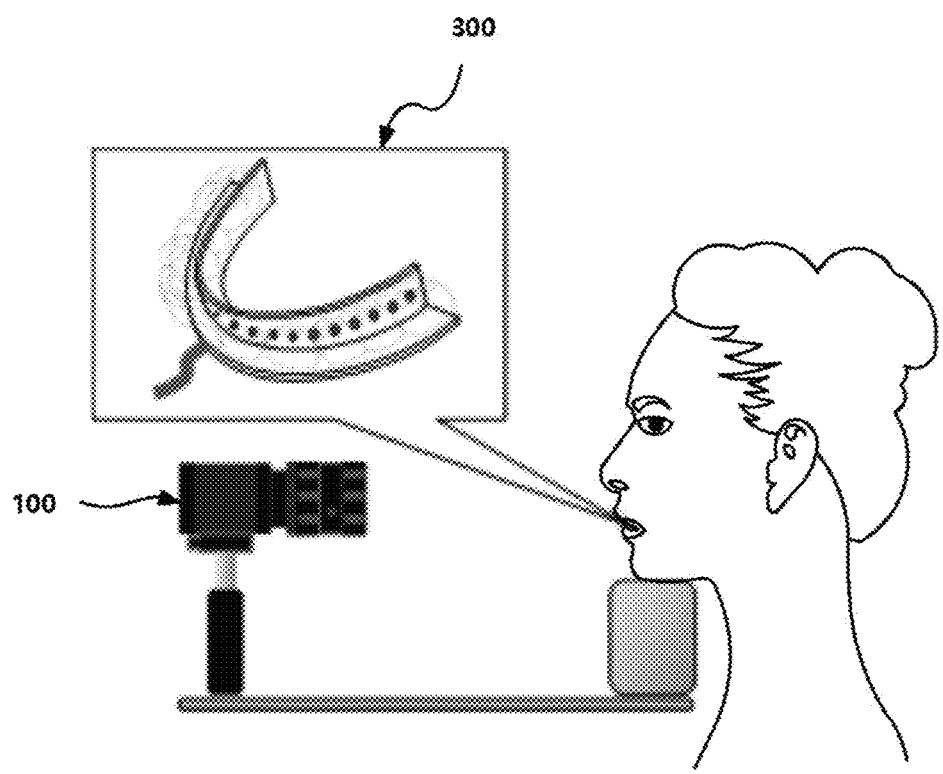
FIG. 2 is a diagram illustrating an application example of an apparatus for acquiring a near-infrared image for dental diagnosis according to the present invention.
Figure 3:
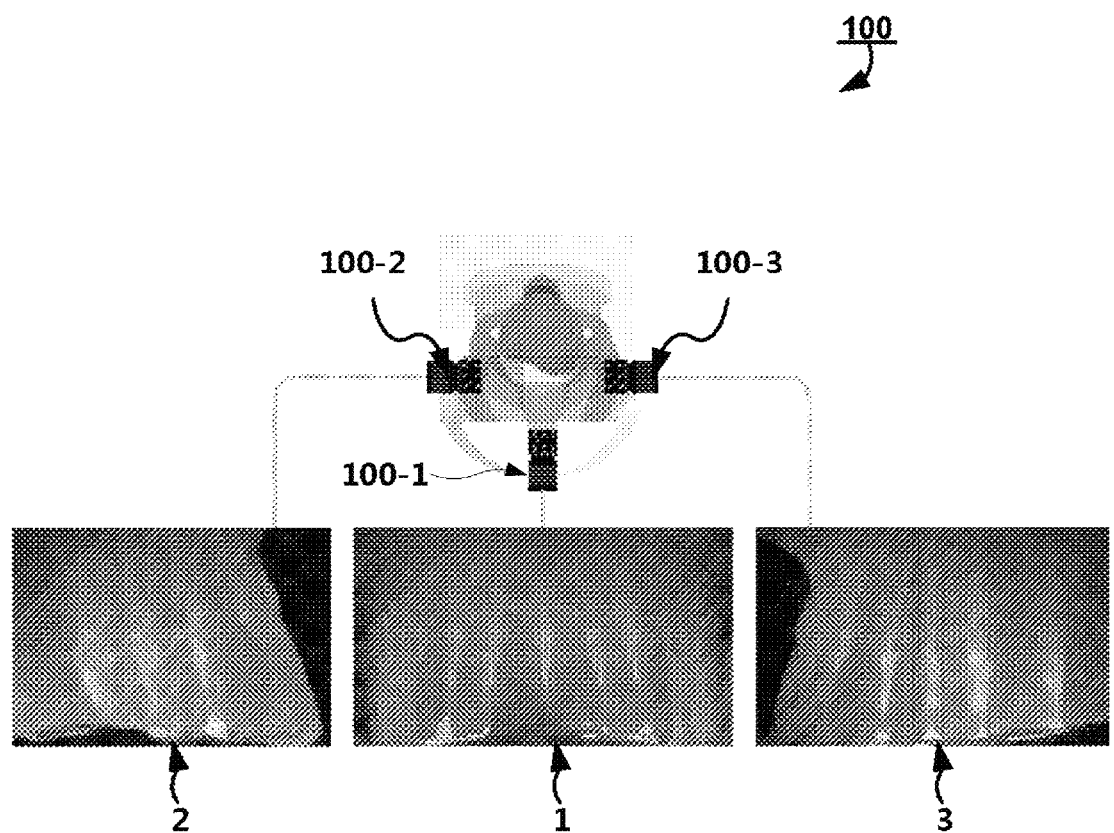
FIG. 3 is a diagram illustrating images acquired by performing photographing from the front, left, and right with an apparatus for acquiring a near-infrared image for dental diagnosis according to an embodiment of the present invention.
Figure 4:
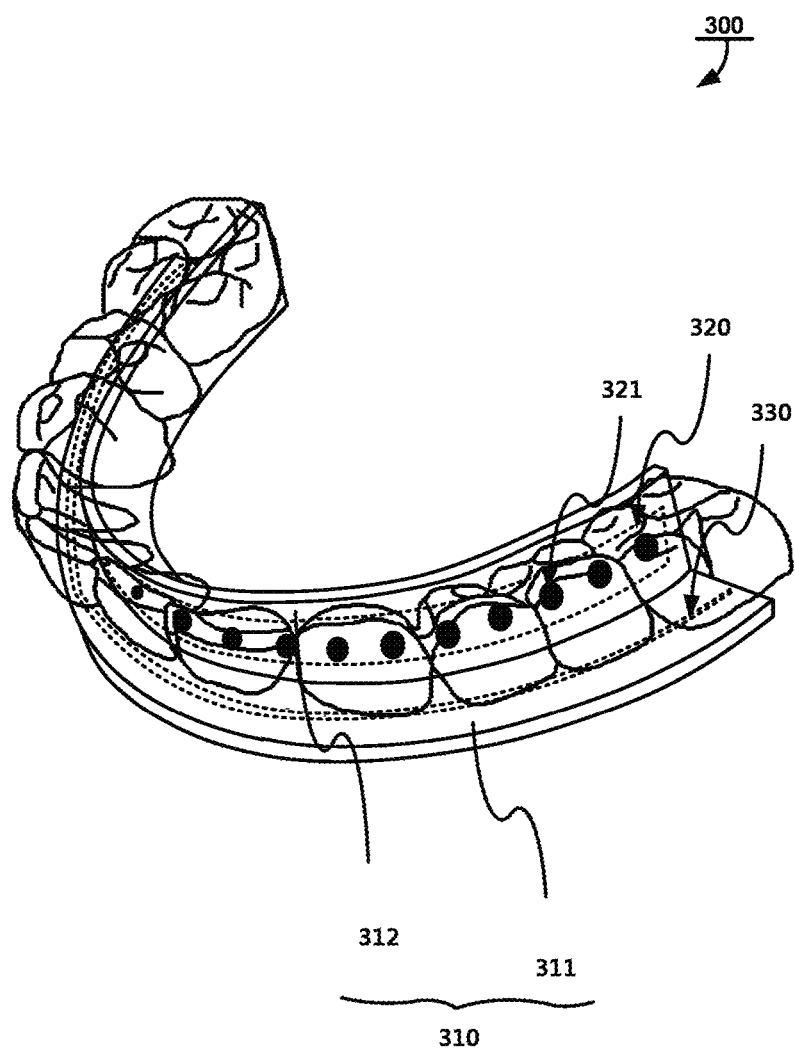
FIG. 4 is a diagram illustrating a physical configuration of a mouthguard-shaped dental diagnosis module of an apparatus for acquiring a near-infrared image for dental diagnosis according to the present invention.

FIG. 1 is a diagram illustrating a configuration of an apparatus for acquiring a near-infrared image for dental diagnosis according to the present invention. FIG. 2 is a diagram illustrating an application example of an apparatus for acquiring a near-infrared image for dental diagnosis according to the present invention. FIG. 3 is a diagram illustrating images acquired by performing photographing from the front, left, and right with an apparatus for acquiring a near-infrared image for dental diagnosis according to an embodiment of the present invention. FIG. 4 is a diagram illustrating a physical configuration of a mouthguard-shaped dental diagnosis module of an apparatus for acquiring a near-infrared image for dental diagnosis according to the present invention. Hereinafter, the description will be made with reference to FIGS. 1 to 4.

An apparatus for acquiring a near-infrared image for dental diagnosis according to the present invention includes: an optical camera 100, a dental diagnosis module 300, and a control module 400; and further includes a camera moving unit 200 according to an embodiment.

The optical camera 100 is placed in front of the patient's face as shown in FIG. 2, and is placed to photograph the vicinity of the mouth of the patient's face. The optical camera photographs a scene in which near-infrared radiation radiated from the inner side of the patient's teeth penetrates toward the outside of the mouth, and outputs the near-infrared image to the control module 400. As shown in FIG. 3, the near-infrared image is an image that is acquired due to different transmittances of teeth, skin tissue, and the like, for near-infrared radiation and clearly shows teeth and periodontal structures.

The dental diagnosis module 300, as shown in FIGS. 2 and 4, includes a mouthguard module frame 310, formed in a shape of a mouthguard, which has a light source composition unit 312 being in contact with a rear surface of the teeth and a sensor composition unit 311 being in contact with a chewing surface of the teeth. The light source composition unit 312 of the mouthguard module frame 310 is provided with a near-infrared light source array 320 in which multiple near-infrared light sources 321 are arranged. The sensor composition unit 311 is provided with a pressure sensor array 330 in which pressure sensors corresponding to the respective teeth are arranged.

When a near-infrared image of an upper teeth arrangement, as shown in FIG. 3, is desired to be acquired, the dental diagnosis module 300 needs to be bitten down on as shown in FIG. 4. When a near-infrared image of a lower teeth arrangement is required to be acquired, the dental diagnosis module needs to be bitten down on in such a manner that the curve is positioned in the reverse direction of the example shown in FIG. 4. Correspondingly, it is preferable that the dental diagnosis module 300 is formed to have elasticity corresponding to the teeth arrangement structure and to be in contact with the rear surface of the teeth arrangement by the elasticity.

The dental diagnosis module 300 may be formed as a hard type having no elasticity. However, in this case, a dental diagnosis module 300 for an upper teeth arrangement and a dental diagnosis module 300 for a lower teeth arrangement need to be provided separately.

The control module 400 includes: a display unit 430 displaying a near-infrared image, a near-infrared teeth arrangement image, a bite pressure image, and the like, and displaying various types of information as at least one among text, an icon, a graphic, and an image; and an input unit 440 provided with at least one button for generating commands such as a photographing command, an image generation command, a modification command, or the like. The control module controls the overall operation of the apparatus for acquiring the near-infrared image for dental diagnosis according to the present invention. The detailed configuration and operation of the control module 400 will be described with reference to FIG. 6.

The camera moving unit 200 is controlled by the control module 400 to reciprocally move the optical camera 100 to the front side, the left side, or the right side of the patient's face as shown in FIG. 3.

Figure 5:
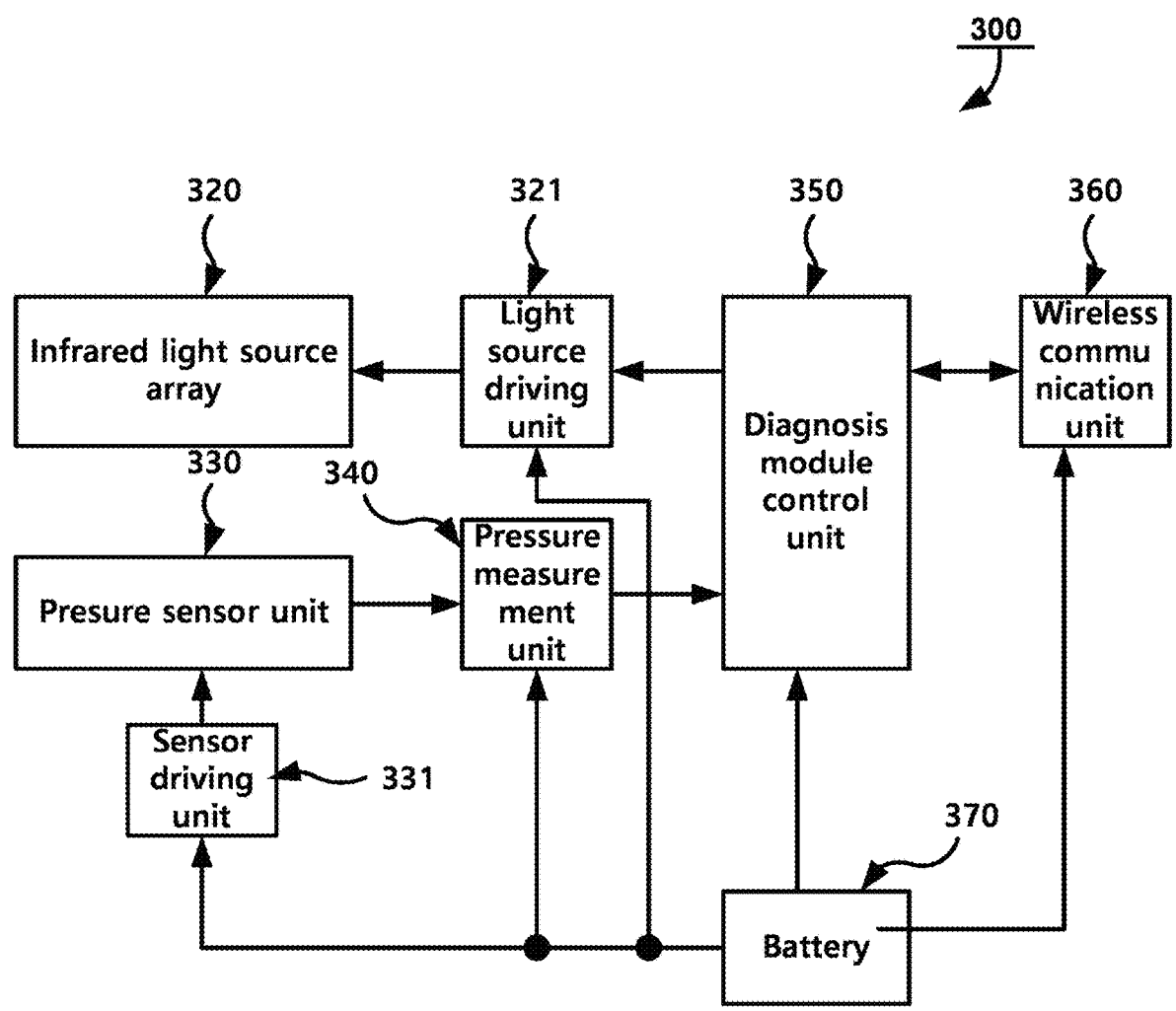
FIG. 5 is a block diagram illustrating a configuration of a dental diagnosis module according to an embodiment of the present invention.

FIG. 5 is a block diagram illustrating a configuration of a dental diagnosis module according to an embodiment of the present invention.

The dental diagnosis module 300 according to the embodiment of the present invention includes only the infrared light source array 320 and the pressure sensor array 330, wherein the infrared light source array 320 receives a light source driving power by the control module 400 to radiate near-infrared radiation, and the pressure sensor array 330 receives a sensor driving power by the control module 400 to provide a pressure signal as a result of pressure to the control module 400. However, in this embodiment, a wired line connecting the dental diagnosis module 300 and the control module 400 needs to be provided, which may result inconvenience for patients and nurses.

To compensate for this, a configuration of the dental diagnosis module 300 in the case of wireless is shown in FIG. 5.

Referring to FIG. 5, the dental diagnosis module 300 according to the embodiment includes: an infrared light source array 320, a light source driving unit 321, a pressure sensor array 330, a sensor driving unit 331, a pressure measurement unit 340, a diagnosis module control unit 350, a wireless communication unit 360, and a battery 370.

The battery 370 supplies source power to the dental diagnosis module 300.

The light source driving unit 321 operates by receiving the source power from the battery 370, and supplies the driving power to each of the near-infrared light sources 321 of the infrared light source array 320 under the control of the diagnosis module control unit 350.

The sensor driving unit 331 receives the source power from the battery 370 and supplies the sensor driving power to each of the pressure sensors of the pressure sensor array 330 under the control of the diagnosis module control unit 350.

The pressure measurement unit 340 converts a pressure signal input from each of the pressure sensors of the pressure sensor array 330 into pressure information and outputs the pressure information to the diagnosis module control unit 350.

The wireless communication unit 360 transmits information, input from the diagnosis module control unit 350, to the control module 400 over a wireless signal, and detects information from a wireless signal received from the control module 400 to output the detected information to the diagnosis module control unit 350.

The diagnosis module control unit 350 drives the light source driving unit 321 and the sensor driving unit 331 to drive the dental diagnosis module 300 when a signal for driving the dental diagnosis module is received from the control module 400 through the wireless communication unit 360. Correspondingly, the diagnosis module control unit transmits the pressure information input from the pressure measurement unit 340 to the control module 400 through the wireless communication unit 360.

Figure 6:
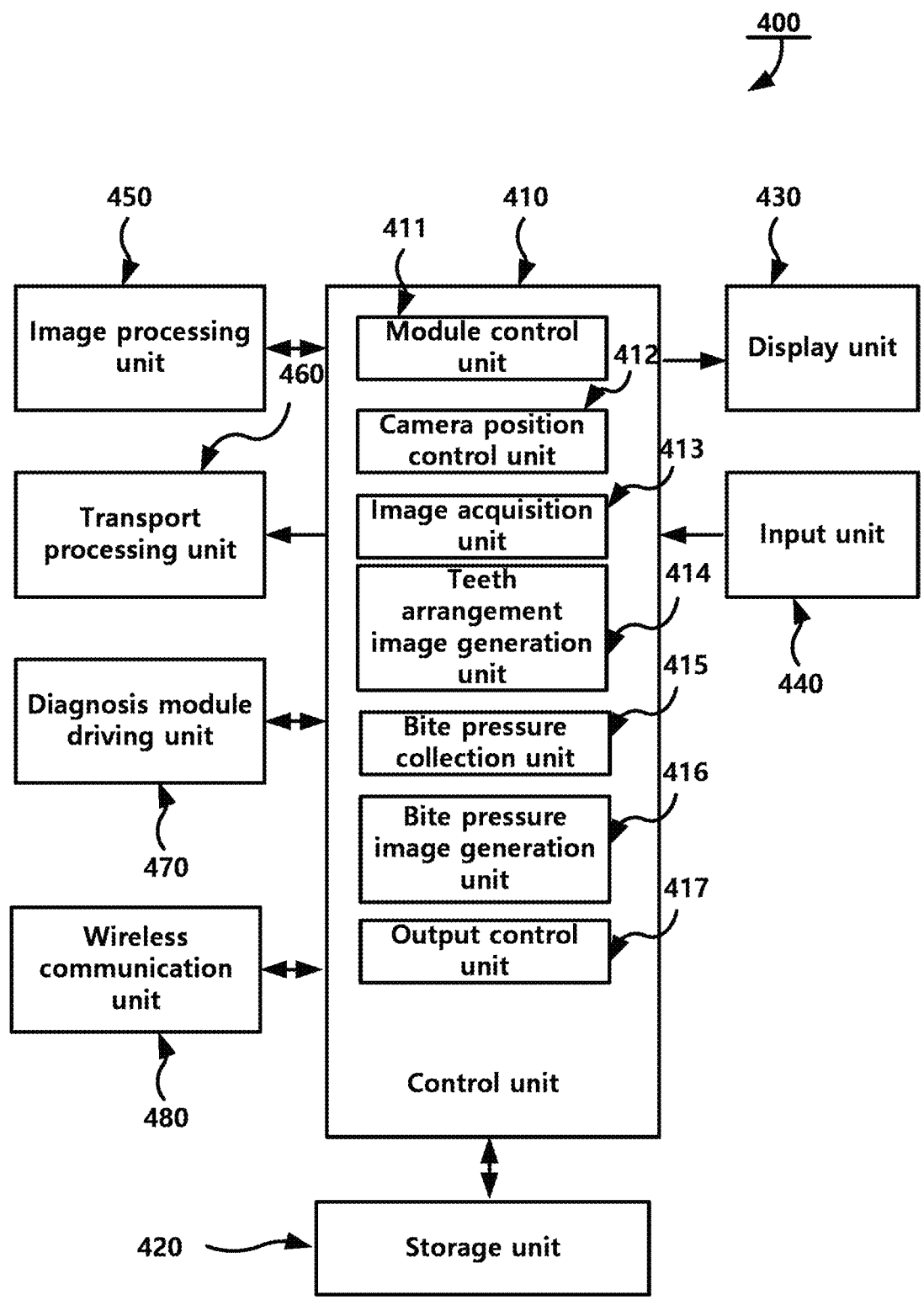
FIG. 6 is a diagram illustrating a detailed configuration of a control module of an apparatus for acquiring a near-infrared image for dental diagnosis according to the present invention.
Figure 7:
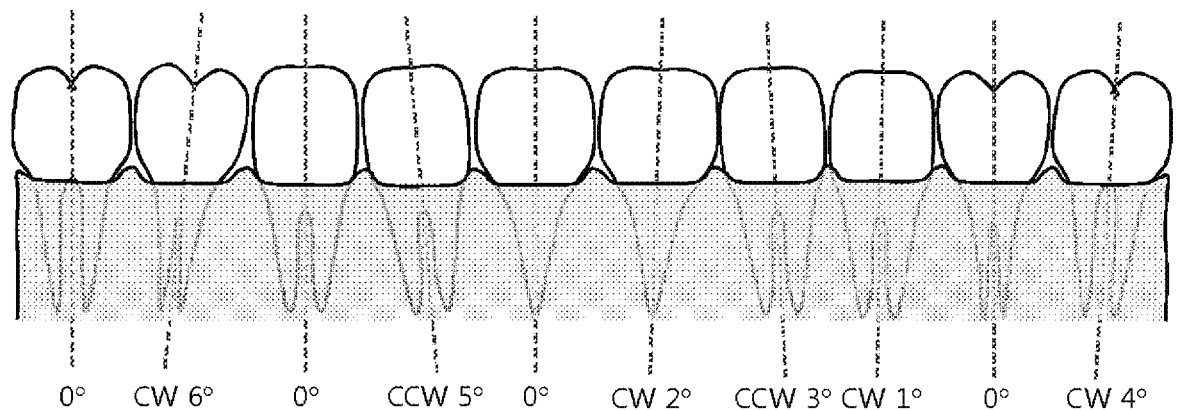
FIG. 7 is a diagram illustrating a bite pressure image which includes bite pressure information obtained by a pressure sensor of a mouthguard-shaped dental diagnosis module according to an embodiment of the present invention.
Figure 8:
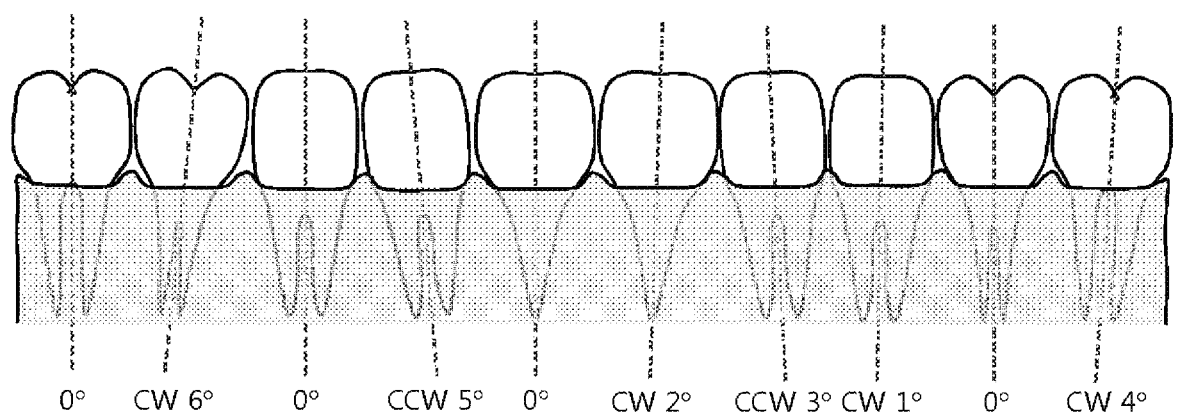
FIG. 8 is a diagram illustrating a teeth/periodontal structure image obtained by constructing acquired images in a panoramic manner according to an embodiment of the present invention.

FIG. 6 is a diagram illustrating a detailed configuration of a control module of an apparatus for acquiring a near-infrared image for dental diagnosis according to the present invention. FIG. 7 is a diagram illustrating a bite pressure image which includes bite pressure information obtained by a pressure sensor of a mouthguard-shaped dental diagnosis module according to an embodiment of the present invention. FIG. 8 is a diagram illustrating a teeth/periodontal structure image obtained by constructing acquired images in a panoramic manner according to an embodiment of the present invention.

Referring to FIGS. 6 to 8, the control module 400 includes a control unit 410, a storage unit 420, a display unit 430, an input unit 440, and an image processing unit 450; and further includes a transport processing unit 460, a diagnosis module driving unit 470, and a wireless communication unit 480 according to an embodiment.

The control unit 410 controls the overall operation of the control module 400 according to the present invention. The detailed configuration of the control unit 410 will be described after describing other components.

The storage unit 420 stores a near-infrared image, a near-infrared teeth arrangement image, a bite pressure image, or the like acquired for each patient.

The display unit 430 displays information as at least one among text, an icon, a graphic, and an image, as described above.

The input unit 440 is provided with multiple buttons for controlling the operation of the control module 400, and outputs a button signal corresponding to the pressed button to the control unit 410. The input unit 440 is integrally formed with a screen of the display unit 430, and may further include a touch pad for outputting, to the control unit 410, a position signal regarding a position that is touched in a manner that corresponds to user interface means displayed on the display unit 430.

The image processing unit 450 outputs a control signal for zooming in/zooming out, photographing, or the like of the optical camera 100 under the control of the control unit 410, correspondingly processes the near-infrared image input from the optical camera 100 in a preset format, and outputs the resulting near-infrared image to the control unit 410. The control signal for zooming in/zooming out, photographing, or the like of the optical camera 100 may be transmitted directly by the control unit 410 to the optical camera 100 rather than through the image processing unit 450.

The transport processing unit 460 controls the camera moving unit 200 under the control of the control unit 410 and outputs a camera movement control signal for controlling a movement direction and a movement distance of the optical camera.

The diagnosis module driving unit 470 is provided when the dental diagnosis module 300 is provided as a wired module according to an embodiment of the present invention. The diagnosis module driving unit is connected to the infrared light source array 320 and the pressure sensor array 330 of the dental diagnosis module 300 in a wired manner, outputs the light source driving power to the infrared light source array 320 under the control of the control unit 410, and provides the sensor driving power to the pressure sensor array 330.

The wireless communication unit 480 is provided when the dental diagnosis module 300 is provided as a wireless module according to an embodiment of the present invention, and performs wireless data communication with the dental diagnosis module 300. As a wireless communication protocol that may apply to the wireless communication unit 480, any one among Bluetooth, Wi-Fi, Zigbee, ultra-wide band (UWB), and the like may apply.

The control unit 410 includes a module control unit 411, a camera position control unit 412, an image acquisition unit 413, a teeth arrangement image generation unit 414, a bite pressure collection unit 415, a bite pressure image generation unit 416, and an output control unit 417, wherein the control unit 410 controls the overall operation of the control module 400 according to the present invention.

Describing specifically, the module control unit 411 controls the overall operation related to the dental diagnosis module 300, and acquires bite pressure information, which is pressure information for each tooth as the result of the control, for storage in the storage unit 420.

The camera position control unit 412 controls the transport processing unit 460 in such a manner that the optical camera 100 is moved to the position corresponding to preset camera position information in response to the command input from the input unit 440.

The image acquisition unit 413 operates the optical camera 100 through the image processing unit 450 to perform photographing in response to the command input from the input unit 440, and acquires the near-infrared image input from the image processing unit 450 after photographing for output. The image acquisition unit 413 outputs a front-side near-infrared image 1, shown in FIG. 3, of the mouth portion photographed from the front side of the patient's face, a left-side near-infrared image 3 of the mouth portion photographed from the left side, and a right-side near-infrared image 2 of the mouth portion photographed from the right side.

The teeth arrangement image generation unit 414 assembles, in a panoramic manner, the front-side near-infrared image 1, the right-side near-infrared image 2, and the left-side near-infrared image 3 acquired from the image acquisition unit 413 so as to generate a near-infrared teeth arrangement image of the upper and/or the lower teeth arrangement and to output the resulting image. The near-infrared teeth arrangement image may be generated in the form of infrared image, which is a combination of the images 1, 2, and 3 shown in FIG. 3, or may be generated in the form of graphic image as shown in FIG. 8.

Further, the teeth arrangement image generation unit 414 may calculate the twisting degree of each tooth and combine the same with the image for display, as shown in FIG. 8.

The bite pressure collection unit 415 collects information on the pressure for each tooth, namely, the bite pressure, through any one among the diagnosis module driving unit 470 and the wireless communication unit 480 according to an embodiment when the dental diagnosis module 300 is driven under the control of the module control unit 410, and outputs the collected information to the bite pressure image generation unit 416.

The bite pressure image generation unit 416 generates a bite pressure image including the bite pressure information for each tooth as shown in FIG. 7 according to the near-infrared teeth arrangement image generated by the teeth arrangement image generation unit 414 and the bite pressure information for each tooth output from the bite pressure collection unit 415.

The output control unit 417 controls the display unit 430 to display information and images generated by the module control unit 411, the camera position control unit 412, the image acquisition unit 413, the teeth arrangement image generation unit 414, the bite pressure collection unit 415, and the bite pressure image generation unit 416.

Figure 9:
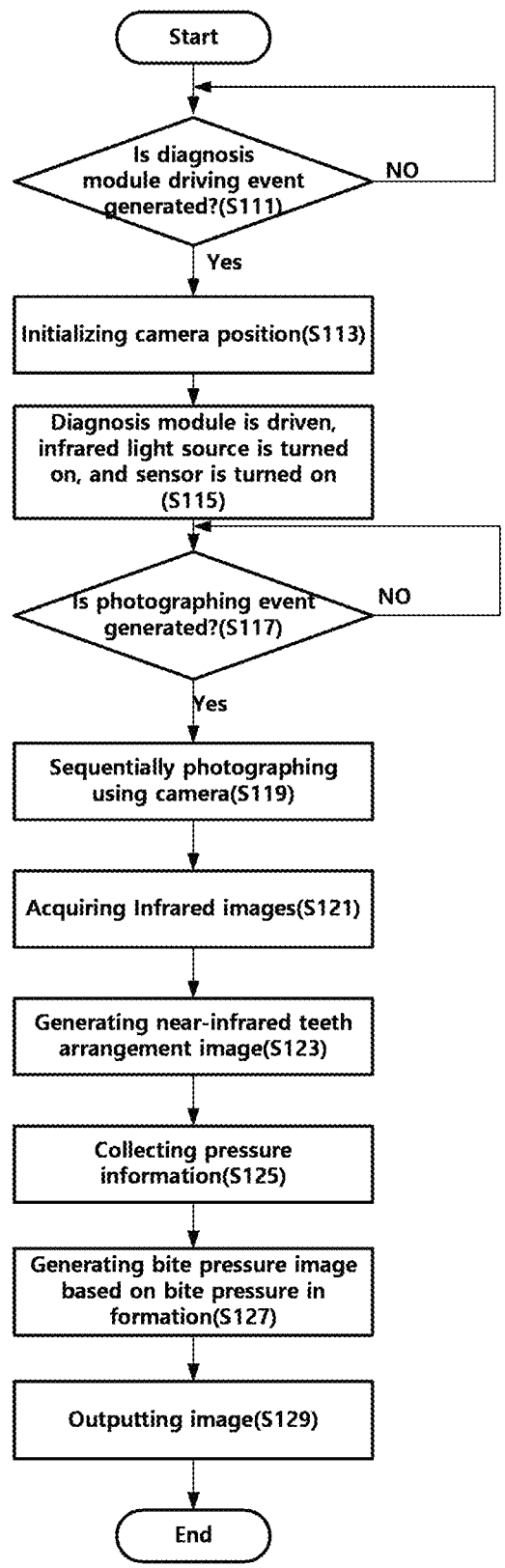
FIG. 9 is a flowchart illustrating a method of acquiring a near-infrared image for dental diagnosis according to the present invention.

FIG. 9 is a flowchart illustrating a method of acquiring a near-infrared image for dental diagnosis according to the present invention.

Referring to FIG. 9, first, the control unit 410 checks whether or not a diagnosis module driving event is generated at step S111. The diagnosis module driving event may be generated by a diagnosis module driving command from the input unit 440.

When the diagnosis module driving event is generated, the control unit 410 controls the transport processing unit 460 through the camera position control unit 412 to perform an initialization process in which the camera moving unit 200 moves the optical camera 100 to an initial position at step S113. The initial position may be any one side among the front side, the left side, and the right side, but preferably is the front side.

When the camera position is initialized, the control unit 410 drives the dental diagnosis module 300 through the module control unit 411 at step S115.

After the dental diagnosis module 300 is driven, the control unit 410 monitors whether or not a photographing event is generated at step S117. When the photographing event is generated, the control unit 410 controls the position of the optical camera 100 sequentially through the camera position control unit 412 and the image acquisition unit 413 so that the front-side near-infrared image 1, the right-side near-infrared image 2, and the left-side near-infrared image 3 for the front side, the left side, and the right side, respectively, are acquired at steps S119 and S121.

When the near-infrared images are acquired, the control unit 410 assembles the front-side near-infrared image 1, the right-side near-infrared image 2, and the left-side near-infrared image in a panoramic manner through the teeth arrangement image generation unit 414 to generate the near-infrared teeth arrangement image at step S123.

After the near-infrared images are acquired or the near-infrared teeth arrangement image is generated, the control unit 410 collects the bite pressure information for each tooth through the bite pressure collection unit 415 at step S125, and generates the bite pressure image based on the generated near-infrared teeth arrangement image and bite pressure information at step S127.

The control unit 410 may output the near-infrared images, the near-infrared teeth arrangement image, and the bite pressure image through the display unit 430 at the time of the acquisition of the same, or may display, on the display unit 430, one or more images selected through the input unit 440 after the final bite pressure image is acquired, at step S129.

In the meantime, the present invention is not limited to the above-described exemplary embodiments, and it will be understood by those skilled in the art that various improvement, modifications, substitutions, and additions may be made without departing from the scope of the present invention. It is noted that if embodiments by such improvements, modifications, substitutions, and additions are within the scope of the following appended claims, the technical ideas thereof are also within the scope of the present invention.

DESCRIPTION OF THE REFERENCE NUMERALS IN THE DRAWINGS

100: optical camera 200: camera moving unit
300: dental diagnosis module 310: dental diagnosis module frame
320: infrared light source array 321: light source driving unit
330: pressure sensor array 331: sensor driving unit
340: pressure measurement unit 350: diagnosis module control unit
360: wireless communication unit 370: battery
400: control module 410: control unit
411: module control unit 412: camera position control unit
413: image acquisition unit 414: a teeth arrangement image generation unit
420: storage unit 430: display unit
440: input unit 450: image processing unit
460: transport processing unit 470: diagnosis module driving unit

The invention claimed is:

1. An apparatus for acquiring a near-infrared image for dental diagnosis, the apparatus comprising:
a dental diagnosis module inserted into a patient's mouth, the dental diagnosis module including a near-infrared light source that is placed along a teeth arrangement in an inner side of the patient's teeth and radiates near-infrared radiation in an outward direction of the patient's mouth;
an optical camera placed in front of a patient's face to photograph the mouth, the optical camera photographing the near-infrared radiation that is radiated from the near-infrared light source and penetrates toward outside of the patient's mouth, and outputting the near-infrared image;
a display unit displaying information as at least one among text, a graphic, and an image;
a processor configured to
generate a near-infrared teeth arrangement image from the near-infrared image, which is inputted from the optical camera,
measure a twist of the teeth and periodontium from the near-infrared teeth arrangement image,
generate a teeth arrangement image including information on the measured twist, and
control the display unit to display the near-infrared teeth arrangement image and the teeth arrangement image.

2. The apparatus of claim 1, wherein the dental diagnosis module is configured to:
be provided in a shape of a mouthguard and include multiple near-infrared light sources on a surface thereof in contact with an inner surface of the teeth; and
be provided with a pressure sensor for each tooth at a portion thereof in contact with a chewing surface of each tooth so as to measure a bite pressure for each tooth of at least one among an upper teeth arrangement and a lower teeth arrangement, and
wherein the processor is further configured to:
further generate a bite pressure image of the upper teeth arrangement and the lower teeth arrangement from the bite pressure and output the bite pressure image.

3. The apparatus of claim 1, wherein the processor is further configured to:
move the optical camera to a front side of the patient's face, from the front side of the patient's face to a left side of the patient's face and to a right side of the patient's face; and
acquire a front-side near-infrared image, a left-side near-infrared image, and a right-side near-infrared image while moving the optical camera to the front side, the left side, and the right side of the patient's face, and construct a panoramic image using the front-side near-infrared image, the left-side near-infrared image, and the right-side near-infrared image so as to generate the near-infrared teeth arrangement image and output the near-infrared teeth arrangement image.

4. The apparatus of claim 3, wherein the processor is further configured to:
process the near-infrared image input from the optical camera in a preset image format and output the processed near-infrared image;
output a driving signal so as to control a movement direction and a movement speed of the optical camera;
output a near-infrared radiation driving signal and a pressure sensor driving signal to the dental diagnosis module, and receive a pressure value for each tooth, which results from the pressure sensor driving signal, from the dental diagnosis module to output the pressure value for each tooth;
receive the front-side near-infrared image, the left-side near-infrared image, and the right-side near-infrared image, construct the panoramic image to generate a dental image, and output the dental image through the display unit; and measure a bite pressure which is the pressure value for each tooth input, generate the bite pressure image for the measured bite pressure, and output the bite pressure image through the display unit.

5. The apparatus of claim 4, wherein the processor is further configured to:
drive the dental diagnosis module;
control a position of the optical camera by according to preset optical camera position information;
acquire, when the dental diagnosis module is driven through the module control unit and the position of the optical camera is set, the front-side near-infrared image, the left-side near-infrared image, and the right-side near-infrared image input through the image processing unit (450) in order of movement of the optical camera, and outputting the front-side, the left-side, and the right-side near-infrared image;
generate the near-infrared teeth arrangement image by assembling the front-side near-infrared image, the left-side near-infrared image, and the right-side near-infrared image, into the panoramic image, and outputting the near-infrared teeth arrangement image;
collect the bite pressure for each tooth through the diagnosis module driving unit; and
generate the bite pressure image based on the bite pressure collected through the bite pressure collection unit and on the near-infrared teeth arrangement image, and outputting the bite pressure image.

6. The apparatus of claim 1, wherein the teeth arrangement diagnosis module includes:
a frame in a shape of a mouthguard, the frame having: a light source composition unit defining a surface of the frame in the shape of the mouthguard, the surface being in contact with an inner surface of the teeth arrangement, and a sensor composition unit defining a surface that is vertically connected with the light source composition unit and is in contact with a chewing surface of tooth of the teeth arrangement;

an infrared light source array including multiple near-infrared light sources arranged on the light source composition unit of the frame, the multiple near-infrared light sources simultaneously radiating near-infrared radiation from an inner side of the mouth in the outward direction;

a pressure sensor array provided on the sensor composition unit of the frame, the pressure sensor measuring a bite pressure, which is a pressure applied by each tooth, and outputting the bite pressure;

a battery provided inside the frame and supplying source power; and wherein the processor is further configured to, transmit a teeth arrangement diagnosis module driving signal in a wireless manner when a teeth arrangement diagnosis module driving event is generated, and receive the bite pressure in a wireless manner to generate a bite pressure image.

7. A method of acquiring a near-infrared image for dental diagnosis, the method comprising:

a dental diagnosis module driving process in which a dental diagnosis module inserted into a patient's mouth is driven and a near-infrared light source placed along a teeth arrangement in an inner side of the patient's teeth is driven to radiate near-infrared radiation;

a near-infrared image acquisition process in which an optical camera placed in front of a patient's face is driven to photograph the near-infrared radiation that is radiated from the inner side of patient's teeth and penetrates, and the near-infrared image is output;

a dental image acquisition process in which a near-infrared teeth arrangement image is generated from the near-infrared image and is output; and a teeth/periodontium twist information generation step in which the near-infrared teeth arrangement image is analyzed to measure a twist of the teeth and periodontium and a near-infrared teeth arrangement image containing teeth and periodontium twist information having a measured twist value of the teeth and the periodontium is generated and is output.

8. The method of claim 7, wherein the dental diagnosis module driving process includes:

a near-infrared radiation step in which an array of multiple near-infrared light sources provided on a surface, which is in contact with an inner surface of the teeth arrangement, of the dental diagnosis module provided in a shape of a mouthguard is driven to radiate the near-infrared radiation from the inner side of the teeth in an outward direction; and a pressure sensor driving step in which a pressure sensor is driven that is provided at a portion of the dental diagnosis module, the portion being in contact with a chewing surface of each tooth, and wherein the image acquisition process includes:

a near-infrared teeth arrangement image acquisition step in which a near-infrared teeth arrangement image is generated from the near-infrared image and is output; and a bite pressure image acquisition step in which bite pressure images of an upper teeth arrangement and a lower teeth arrangement are generated from a bite pressure and are output.

9. The method of claim 8, wherein the image acquisition process includes:

a front-side photographing step in which the optical camera is positioned in front of the patient and photographs the near-infrared radiation at a front side of the patient; and a flank-side photographing step in which the optical camera is moved to left and right sides sequentially and photographs the near-infrared radiation with respect to each of the left side and the right side, and wherein at the near-infrared teeth image acquisition step, the front-side, left-side, and right-side near-infrared images are assembled in a panoramic manner to generate and output the near-infrared teeth arrangement image.

* * * * *